United States Patent
Higgins et al.

(10) Patent No.: US 10,052,122 B2
(45) Date of Patent: Aug. 21, 2018

(54) SPIN-TO-OPEN ATHERECTOMY DEVICE WITH ELECTRIC MOTOR CONTROL

(71) Applicant: Cardiovascular Systems, Inc., St. Paul, MN (US)

(72) Inventors: Joseph P. Higgins, Minnetonka, MN (US); Victor L. Schoenle, Greenfield, MN (US); Michael J. Grace, Brooklyn Park, MN (US); Matthew D. Cambronne, St. Anthony, MN (US); Robert E. Kohler, Lake Elmo, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 271 days.

(21) Appl. No.: 14/597,932

(22) Filed: Jan. 15, 2015

(65) Prior Publication Data
US 2015/0201956 A1 Jul. 23, 2015

Related U.S. Application Data

(60) Provisional application No. 61/928,536, filed on Jan. 17, 2014.

(51) Int. Cl.
*A61B 17/3207* (2006.01)
*A61B 17/00* (2006.01)
(Continued)

(52) U.S. Cl.
CPC .. *A61B 17/3207* (2013.01); *A61B 17/320758* (2013.01); *A61B 2017/00017* (2013.01);
(Continued)

(58) Field of Classification Search
CPC ........ A61B 17/3207; A61B 17/210758; A61B 2017/00017; A61B 2017/0123
See application file for complete search history.

(56) References Cited

U.S. PATENT DOCUMENTS

| 3,000,197 A | 9/1961 | Ruegg et al. |
| 3,177,684 A | 4/1965 | Bossier, Jr. |

(Continued)

FOREIGN PATENT DOCUMENTS

| DE | 4334266 | 4/1994 |
| JP | 509117 | 10/1995 |

(Continued)

OTHER PUBLICATIONS

Notification Concerning Transmittal of International Preliminary Report on Patentability and International Jreliminary Report on Patentability issued in related PCT application No. PCT/US2015/011744, dated Jul. 28, 2016.

*Primary Examiner* — Alexander Orkin
(74) *Attorney, Agent, or Firm* — Barnes & Thornburg LLP; Jeffrey R. Stone

(57) ABSTRACT

A rotational atherectomy system is disclosed, comprising: an elongated, flexible spin-to-open drive shaft having a distal end for insertion into a vasculature of a patient and having a proximal end opposite the distal end remaining outside the vasculature of the patient; a concentric or eccentric abrasive element, preferably a solid crown, attached to the drive shaft proximate the distal end of the drive shaft; an electric motor rotatably coupled to the proximal end of the drive shaft, the electric motor being capable of rotating the drive shaft in a spin-to-open direction; and control electronics for monitoring and controlling the rotation of the electric motor. When an obstruction at the distal end is detected by the applied torque and/or current reaching a predetermined maximum allowed level and with the drive shaft opened to a maximum allowed outer diameter, power to the motor is eliminated.

8 Claims, 9 Drawing Sheets

(51) Int. Cl.
 *A61B 17/22* (2006.01)
 *A61B 17/32* (2006.01)
 *A61B 90/00* (2016.01)

(52) U.S. Cl.
 CPC .............. *A61B 2017/00123* (2013.01); *A61B 2017/00199* (2013.01); *A61B 2017/00398* (2013.01); *A61B 2017/22045* (2013.01); *A61B 2017/320004* (2013.01); *A61B 2017/320032* (2013.01); *A61B 2017/320766* (2013.01); *A61B 2090/066* (2016.02); *A61B 2090/0801* (2016.02)

(56) References Cited

U.S. PATENT DOCUMENTS

| | | |
|---|---|---|
| 3,374,425 A | 3/1968 | Barditch et al. |
| 4,304,511 A | 12/1981 | Machida |
| 4,932,419 A | 6/1990 | de Toledo |
| 4,951,677 A | 8/1990 | Crowley et al. |
| 4,979,951 A | 12/1990 | Simpson |
| 5,026,384 A | 6/1991 | Farr et al. |
| 5,052,404 A | 10/1991 | Hodgson |
| 5,078,723 A | 1/1992 | Dance et al. |
| 5,100,425 A | 3/1992 | Fischell et al. |
| 5,103,543 A | 4/1992 | Hodgson |
| 5,115,814 A | 5/1992 | Griffith et al. |
| 5,154,705 A | 10/1992 | Fleischhacker et al. |
| 5,158,564 A | 10/1992 | Schnepp-Pesch et al. |
| 5,165,421 A | 11/1992 | Fleischhacker et al. |
| 5,217,478 A | 6/1993 | Rexroth |
| 5,243,988 A | 9/1993 | Sieben et al. |
| 5,257,996 A | 11/1993 | McGuire |
| 5,261,877 A | 11/1993 | Fine et al. |
| 5,314,438 A | 5/1994 | Shturman |
| 5,336,167 A | 8/1994 | Sullivan et al. |
| 5,353,798 A | 10/1994 | Sieben |
| 5,356,418 A | 10/1994 | Shturman |
| 5,358,509 A | 10/1994 | Fine et al. |
| 5,360,432 A | 11/1994 | Shturman |
| 5,366,457 A | 11/1994 | McGuire et al. |
| 5,368,035 A | 11/1994 | Hamm et al. |
| 5,370,651 A | 12/1994 | Summers |
| 5,372,138 A | 12/1994 | Crowley et al. |
| 5,373,619 A | 12/1994 | Fleischhacker et al. |
| 5,374,270 A | 12/1994 | McGuire et al. |
| 5,391,169 A | 2/1995 | McGuire |
| 5,391,170 A | 2/1995 | McGuire et al. |
| 5,421,338 A | 6/1995 | Crowley et al. |
| 5,423,740 A | 6/1995 | Sullivan et al. |
| 5,431,673 A | 7/1995 | Summers et al. |
| 5,437,282 A | 8/1995 | Koger et al. |
| 5,438,997 A | 8/1995 | Sieben et al. |
| 5,445,155 A | 8/1995 | Sieben |
| 5,464,407 A | 11/1995 | McGuire |
| 5,490,859 A | 2/1996 | Mische et al. |
| 5,501,694 A | 3/1996 | Ressemann et al. |
| 5,520,693 A | 5/1996 | McGuire et al. |
| 5,522,875 A | 6/1996 | Gates et al. |
| 5,524,630 A | 6/1996 | Crowley |
| 5,540,681 A | 7/1996 | Strul et al. |
| 5,540,707 A | 7/1996 | Ressemann et al. |
| 5,546,948 A | 8/1996 | Hamm et al. |
| 5,562,275 A | 10/1996 | Weissenfluh et al. |
| 5,562,669 A | 10/1996 | McGuire |
| 5,571,088 A | 11/1996 | Lennox et al. |
| 5,575,772 A | 11/1996 | Lennox |
| 5,588,432 A | 12/1996 | Crowley |
| 5,627,710 A | 5/1997 | Schoeffler |
| 5,630,823 A | 5/1997 | Schmitz-Rode et al. |
| 5,630,837 A | 5/1997 | Crowley |
| 5,678,296 A | 10/1997 | Fleischhacker et al. |
| 5,681,320 A | 10/1997 | McGuire |
| 5,683,400 A | 11/1997 | McGuire |
| 5,715,825 A | 2/1998 | Crowley |
| 5,746,758 A | 5/1998 | Nordgren et al. |
| 5,792,157 A | 8/1998 | Mische et al. |
| 5,797,918 A | 8/1998 | McGuire et al. |
| 5,803,812 A | 9/1998 | Kakiuchi et al. |
| 5,816,923 A | 10/1998 | Milo et al. |
| 5,836,868 A | 11/1998 | Ressemann et al. |
| 5,840,031 A | 11/1998 | Crowley |
| 5,860,974 A | 1/1999 | Abele |
| 5,865,834 A | 2/1999 | McGuire |
| 5,897,567 A | 4/1999 | Ressemann et al. |
| 5,921,956 A | 7/1999 | Grinberg et al. |
| 5,932,035 A | 8/1999 | Koger et al. |
| 5,938,672 A | 8/1999 | Nash |
| 6,004,269 A | 12/1999 | Crowley et al. |
| 6,027,460 A | 2/2000 | Shturman |
| 6,050,949 A | 4/2000 | White et al. |
| 6,165,127 A | 12/2000 | Crowley |
| 6,210,395 B1 | 4/2001 | Fleischhacker et al. |
| 6,217,595 B1 | 4/2001 | Shturman et al. |
| 6,258,111 B1 | 7/2001 | Ross et al. |
| 6,280,332 B1 | 8/2001 | Knutson |
| 6,352,538 B2 | 3/2002 | McGuire et al. |
| 6,364,840 B1 | 4/2002 | Crowley |
| 6,364,841 B1 | 4/2002 | White et al. |
| 6,398,755 B1 | 6/2002 | Belef et al. |
| 6,419,644 B1 | 7/2002 | White et al. |
| 6,443,903 B1 | 9/2002 | White et al. |
| 6,447,443 B1 | 9/2002 | Keogh et al. |
| 6,454,717 B1 | 9/2002 | Pantages et al. |
| 6,494,890 B1 * | 12/2002 | Shturman ...... A61B 17/320758 606/159 |
| 6,503,261 B1 | 1/2003 | Bruneau et al. |
| 6,565,588 B1 | 5/2003 | Clement et al. |
| 6,572,553 B2 | 6/2003 | Crowley |
| 6,572,555 B2 | 6/2003 | White et al. |
| 6,585,655 B2 | 7/2003 | Crowley |
| 6,620,113 B2 | 9/2003 | White et al. |
| 6,626,852 B2 | 9/2003 | White et al. |
| 6,626,853 B2 | 9/2003 | White et al. |
| 6,641,546 B2 | 11/2003 | White et al. |
| 6,669,662 B1 | 12/2003 | Webler |
| 6,685,696 B2 | 2/2004 | Fleischhacker et al. |
| 6,758,818 B2 | 7/2004 | Pantages et al. |
| 6,793,634 B2 | 9/2004 | White et al. |
| 6,818,001 B2 | 11/2004 | Wulfman et al. |
| 6,827,693 B2 | 12/2004 | White et al. |
| 6,878,150 B1 | 4/2005 | McGuire et al. |
| 6,936,056 B2 | 8/2005 | Nash et al. |
| 6,958,071 B2 | 10/2005 | Carusillo et al. |
| 7,025,770 B2 | 4/2006 | McGuire et al. |
| 7,037,271 B2 | 5/2006 | Crowley |
| 7,044,915 B2 | 5/2006 | White et al. |
| 7,344,546 B2 | 3/2008 | Wulfman et al. |
| 7,485,127 B2 | 2/2009 | Nistal |
| 7,674,272 B2 | 3/2010 | Torrance et al. |
| 7,713,231 B2 | 5/2010 | Wulfman et al. |
| 7,815,510 B2 | 10/2010 | Asbeck et al. |
| 8,323,240 B2 | 12/2012 | Wulfman et al. |
| 8,475,484 B2 | 7/2013 | Wulfman et al. |
| 2001/0016746 A1 | 8/2001 | McGuire et al. |
| 2001/0021831 A1 | 9/2001 | Fleischhacker et al. |
| 2001/0037073 A1 | 11/2001 | White et al. |
| 2002/0007190 A1 | 1/2002 | Wulfman et al. |
| 2002/0026128 A1 | 2/2002 | White et al. |
| 2002/0026129 A1 | 2/2002 | White et al. |
| 2002/0058956 A1 | 5/2002 | Honeycutt et al. |
| 2002/0062085 A1 | 5/2002 | White et al. |
| 2002/0099289 A1 | 7/2002 | Crowley |
| 2002/0147414 A1 | 10/2002 | White et al. |
| 2002/0151799 A1 | 10/2002 | Pantages et al. |
| 2002/0151800 A1 | 10/2002 | White et al. |
| 2002/0188201 A1 | 12/2002 | Crowley |
| 2002/0188225 A1 | 12/2002 | White et al. |
| 2002/0188226 A1 | 12/2002 | White et al. |
| 2003/0009173 A1 | 1/2003 | McGuire et al. |
| 2003/0125717 A1 | 7/2003 | Whitman |
| 2003/0139689 A1 | 7/2003 | Shturman et al. |
| 2003/0208119 A1 | 11/2003 | Crowley |
| 2004/0006358 A1 | 1/2004 | Wulfman et al. |

(56) References Cited

U.S. PATENT DOCUMENTS

| | | |
|---|---|---|
| 2004/0019279 A1 | 1/2004 | White et al. |
| 2004/0097995 A1 | 5/2004 | Nash et al. |
| 2004/0181249 A1 | 9/2004 | Torrance et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0235611 A1 | 11/2004 | Nistal |
| 2004/0236312 A1 | 11/2004 | Nistal et al. |
| 2004/0243162 A1 | 12/2004 | Wulfman et al. |
| 2006/0020282 A1 | 1/2006 | Henniges et al. |
| 2006/0184186 A1 | 8/2006 | Noone |
| 2007/0060395 A1 | 3/2007 | Asbeck et al. |
| 2007/0225739 A1 | 9/2007 | Pintor et al. |
| 2007/0239140 A1 | 10/2007 | Chechelski et al. |
| 2007/0239182 A1 | 10/2007 | Glines et al. |
| 2007/0270688 A1 | 11/2007 | Gelbart et al. |
| 2007/0282358 A1 | 12/2007 | Remiszewski et al. |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0103446 A1 | 1/2008 | Torrance et al. |
| 2008/0030649 A1 | 2/2008 | Choi et al. |
| 2008/0045986 A1 | 2/2008 | To et al. |
| 2008/0058846 A1 | 3/2008 | Vosough |
| 2008/0065125 A1 | 3/2008 | Olson |
| 2008/0097500 A1 | 4/2008 | Nash et al. |
| 2008/0140101 A1 | 6/2008 | Carley et al. |
| 2008/0221601 A1 | 9/2008 | Huynh et al. |
| 2008/0228208 A1 | 9/2008 | Wulfman et al. |
| 2008/0269789 A1 | 10/2008 | Eli |
| 2008/0306498 A1 | 12/2008 | Thatcher et al. |
| 2010/0121361 A1* | 5/2010 | Plowe ............ A61B 17/320758 606/159 |
| 2010/0125276 A1 | 5/2010 | Palermo |
| 2011/0112562 A1 | 5/2011 | Torrance |
| 2011/0213391 A1* | 9/2011 | Rivers ............ A61B 17/320758 606/159 |
| 2012/0029282 A1 | 2/2012 | Yamakawa et al. |
| 2012/0029283 A1 | 2/2012 | Yamakawa et al. |
| 2012/0172656 A1 | 7/2012 | Walters et al. |
| 2012/0265002 A1 | 10/2012 | Roehn et al. |
| 2013/0165908 A1 | 6/2013 | Purdy et al. |

FOREIGN PATENT DOCUMENTS

| | | |
|---|---|---|
| JP | 2002279149 | 9/2002 |
| JP | 2002538927 | 11/2002 |
| JP | 2004508096 | 3/2004 |
| JP | 2006514577 | 5/2006 |
| JP | 2008200513 | 4/2008 |
| JP | 2008521503 | 6/2008 |
| WO | WO2000/56230 | 9/2000 |
| WO | WO2006/126076 | 11/2006 |
| WO | 2013056262 A1 | 4/2013 |
| WO | 2013142232 A1 | 9/2013 |

* cited by examiner

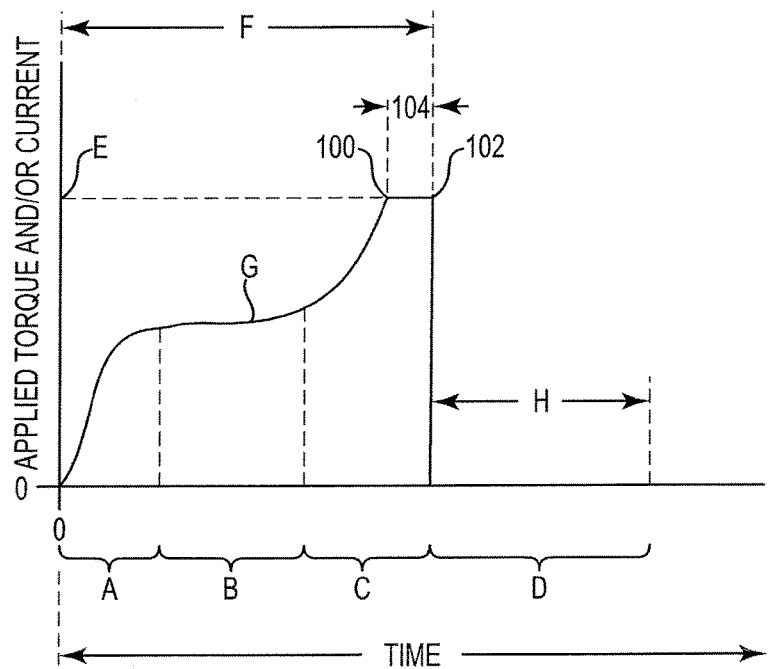

LEGEND

A: ELECTRIC MOTOR ACCELERATES DRIVE SHAFT TO DESIRED ROTATIONAL SPEED.

B: DRIVE SHAFT AT DESIRED ROTATIONAL SPEED WITH NOMINAL OUTER DIAMETER.

C: AFTER ENCOUNTERING AN OBSTRUCTION, DRIVE SHAFT OPENS TO MAXIMUM OUTER DIAMETER (100) AND APPLIED TORQUE AND CURRENT IS AT MAXIMUM.

D: AFTER POWER IS ELIMINATED TO ELECTRIC MOTOR, DRIVE SHAFT OUTER DIAMETER RETURNS TO NOMINAL OUTER DIAMETER.

E: MAXIMUM APPLIED TORQUE AND/OR CURRENT

F: DRIVE SHAFT RPM CONSTANT.

G: OBSTRUCTION ENCOUNTERED.

H: NO TORQUE INDUCED ROTATION.

Fig. 12

SPIN-TO-OPEN ATHERECTOMY DEVICE WITH ELECTRIC MOTOR CONTROL

CROSS-REFERENCE TO RELATED APPLICATIONS

This application claims priority to App. Ser. No. 61/928,536, entitled "Spin-to-Open Atherectomy Device with Electric Motor", filed Jan. 17, 2014.

STATEMENT REGARDING FEDERALLY SPONSORED RESEARCH OR DEVELOPMENT

Not Applicable

FIELD OF THE INVENTION

The invention relates to devices and methods for removing tissue from body passageways, such as removal of atherosclerotic plaque from arteries, utilizing a rotational atherectomy device. In particular, the invention relates to improvements in a rotational atherectomy device having a drive shaft arranged to open to a larger diameter when loaded and wherein the torque delivered from the electric motor to the drive shaft is controlled by a controller.

BACKGROUND OF THE INVENTION

Description of the Related Art

Atherectomy is a non-surgical procedure to open blocked coronary arteries or vein grafts by using a device on the end of a catheter to cut or shave away atherosclerotic plaque (a deposit of fat and other substances that accumulate in the lining of the artery wall). For the purposes of this application, the term "abrading" is used to describe the grinding and/or scraping action of such an atherectomy head.

Atherectomy is performed to restore the flow of oxygen-rich blood to the heart, to relieve chest pain, and to prevent heart attacks. It may be done on patients with chest pain who have not responded to other medical therapy and on certain of those who are candidates for balloon angioplasty (a surgical procedure in which a balloon catheter is used to flatten plaque against an artery wall) or coronary artery bypass graft surgery. It is sometimes performed to remove plaque that has built up after a coronary artery bypass graft surgery.

Atherectomy uses a rotating shaver or other device placed on the end of a catheter to slice away or destroy plaque. At the beginning of the procedure, medications to control blood pressure, dilate the coronary arteries, and prevent blood clots are administered. The patient is awake but sedated. The catheter is inserted into an artery in the groin, leg, or arm, and threaded through the blood vessels into the blocked coronary artery. The cutting head is positioned against the plaque and activated, and the plaque is ground up or suctioned out.

The types of atherectomy are rotational, directional, and transluminal extraction. Rotational atherectomy uses a high speed rotating shaver to grind up plaque. Directional atherectomy was the first type approved, but is no longer commonly used; it scrapes plaque into an opening in one side of the catheter. Transluminal extraction coronary atherectomy uses a device that cuts plaque off vessel walls and vacuums it into a bottle. It is used to clear bypass grafts.

Performed in a cardiac catheterization lab, atherectomy is also called removal of plaque from the coronary arteries. It can be used instead of, or along with, balloon angioplasty.

Several devices have been disclosed that perform rotational atherectomy. For instance, U.S. Pat. No. 5,360,432, issued on Nov. 1, 1994 to Leonid Shturman, and titled "Abrasive drive shaft device for directional rotational atherectomy" discloses an abrasive drive shaft atherectomy device for removing stenotic tissue from an artery, and is incorporated by reference herein in its entirety. The device includes a rotational atherectomy apparatus having a flexible, elongated drive shaft having a central lumen and a segment, near its distal end, coated with an abrasive material to define an abrasive segment. At sufficiently high rotational speeds, the abrasive segment expands radially, and can sweep out an abrading diameter that is larger than its rest diameter. In this manner, the atherectomy device may remove a blockage that is larger than the catheter itself. Use of an expandable head is an improvement over atherectomy devices that use non-expandable heads; such non-expandable devices typically require removal of particular blockages in stages, with each stage using a differently-sized head.

U.S. Pat. No. 5,314,438 (Shturman) shows another atherectomy device having a rotatable drive shaft with a section of the drive shaft having an enlarged diameter, at least a segment of this enlarged diameter section being covered with an abrasive material to define an abrasive segment of the drive shaft. When rotated at high speeds, the abrasive segment is capable of removing stenotic tissue from an artery.

A typical atherectomy device includes a single-use disposable portion, which can be attached and detached from a non-disposable control unit (also referred to as a controller). The disposable portion includes elements that are exposed to saline and to the bodily fluids of the patient, such as a handle, a catheter, a rotatable drive shaft, and an abrasive head. The handle includes a turbine that rotates the drive shaft, and a knob that can longitudinally advance and retract the drive shaft along the catheter. Often, the device has a foot switch that activates the handle.

Typical atherectomy devices use pneumatic power to drive the drive shaft, with the controller managing the amount of compressed air that is delivered to the turbine in the handle. The compressed air spins the turbine that, in turn, spins the drive shaft, and spins an abrasive crown attached to the drive shaft. Orbiting motion of the crown enlarges and widens the channel opening of a restricted or blocked vascular vessel.

The pneumatic system required for such a device is substantial. For instance, a typical pneumatic system requires compressed air or nitrogen, with a minimum pressure of 100 pounds per square inch (689,000 pascals, or 6.8 atmospheres), and a minimum flow volume rate of 4 cubic feet per minute (113 liters per minute, or 1.9 liters per second). The controller for such an air system is mechanically complicated, and can be quite expensive.

BRIEF SUMMARY OF THE INVENTION

An embodiment is a rotational atherectomy system, comprising: an elongated, flexible spin-to-open drive shaft having a distal end for insertion into a vasculature of a patient and having a proximal end opposite the distal end remaining outside the vasculature of the patient; a concentric or eccentric abrasive element, preferably a solid crown, attached to the drive shaft proximate the distal end of the drive shaft; an electric motor rotatably coupled to the proximal end of the drive shaft, the electric motor being capable of rotating the drive shaft in a spin-to-open direction; and control electronics for monitoring and controlling the rotation of the electric motor, including in some embodiments detecting when an obstruction has been encountered with subsequent elimination of power to the drive shaft.

Another embodiment is a rotational atherectomy system, comprising: an elongated, flexible spin-to-open drive shaft having a distal end for insertion into a vasculature of a patient and having a proximal end opposite the distal end remaining outside the vasculature of the patient; an eccentric solid crown attached to the drive shaft proximate the distal end of the drive shaft; an electric motor rotatably coupled to the proximal end of the drive shaft, the electric motor being capable of rotating the drive shaft in a spin-to-open direction; a handle housing the electric motor; control electronics for monitoring and controlling the rotation of the electric motor, the control electronics including an algorithm that detects and controls when the drive shaft and eccentric solid crown encounter a blockage in the vasculature with subsequent elimination of power to the electric motor.

Yet another embodiment is a rotational atherectomy system, comprising: an elongated, flexible spin-to-open drive shaft having a distal end for insertion into a vasculature of a patient and having a proximal end opposite the distal end remaining outside the vasculature of the patient; an eccentric solid crown attached to the drive shaft proximate the distal end of the drive shaft; an electric motor rotatably coupled to the proximal end of the drive shaft, the electric motor being capable of rotating the drive shaft in a spin-to-open direction; and control electronics for monitoring and controlling the rotation of the electric motor. The drive shaft and eccentric solid crown, when rotating, have a torque limited by a current supplied to the electric motor. The control electronics include an algorithm that detects and controls when the drive shaft and eccentric solid crown encounter a blockage in the vasculature that rapidly slows their rotation. The control electronics include limits on maximum and minimum rotational speeds of the electric motor. The control electronics also include limits on maximum and minimum current supplied to the electric motor and limits on maximum and minimum torque delivered by the electric motor.

In all embodiments, the spin-to-open drive shaft will open if blocked from rotating or during a loading event, causing the drive shaft's outer diameter to increase and the length of the drive shaft to shorten.

In addition, the various embodiments of the present invention represent improvements to the known systems. The control electronics will eliminate power to the electric motor when the maximum allowed outer diameter, correspondent to maximum applied torque and/or maximum current and/or minimum rotational speed is reached.

For example, opening of the drive shaft during loading events helps translate torque to the electric motor, thereby allowing better more accurate torque monitoring by the control electronics. Additionally, the opening drive shaft during loading decreases the length of the drive shaft itself, reducing the overall loading of the drive shaft during loading events. Further, the opening of the drive shaft during a loading event reduces the friction of the system on the guidewire, reducing the possibility that the system guidewire may be damaged during the loading event.

BRIEF DESCRIPTION OF THE SEVERAL VIEWS OF THE DRAWINGS

FIG. 12 is a plot of torque and/or current vs time during a distal end obstruction event for the electric motor with a spin-to-open drive shaft.

DETAILED DESCRIPTION OF THE INVENTION

Figure 1:
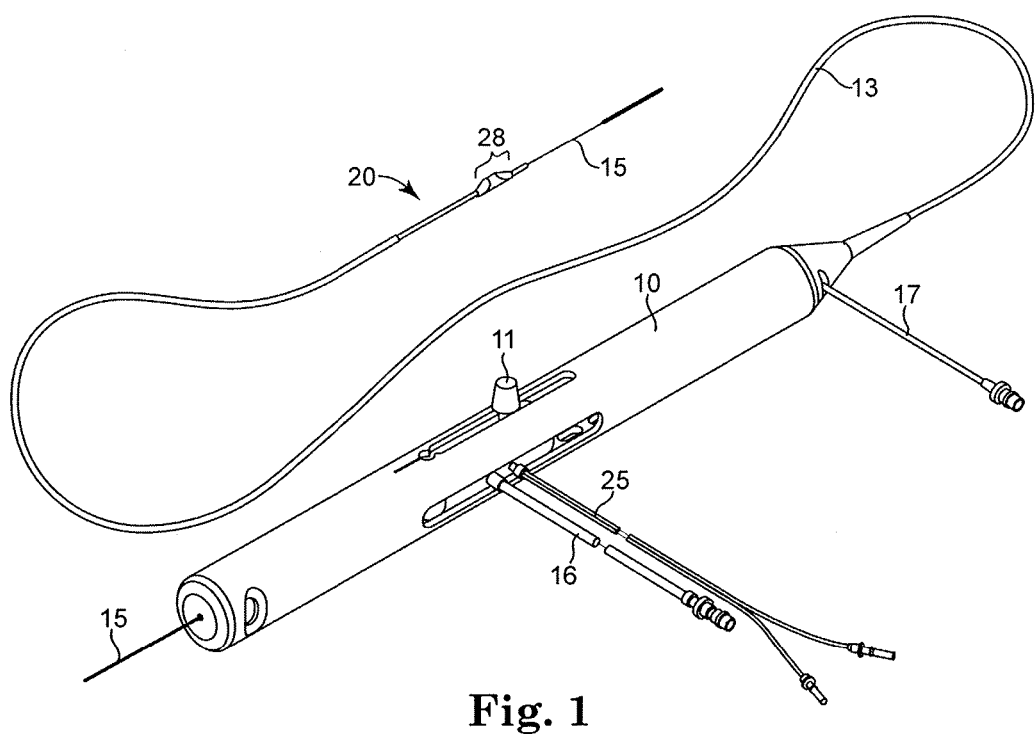
FIG. 1 is a perspective view of a known rotational atherectomy device.

An atherectomy device is disclosed, which is rotationally driven by an electric motor. The device includes features unavailable on gas turbine-driven systems, such as the storing in memory of low/medium/high preset rotation speeds for particular models of handle, calculations of the amount of saline left in the IV and associated warnings when it gets sufficiently low, and automatic adjustment of the IV pump rate to a predetermined or calculated level when the rotational speed of the motor is changed. The electric motor has far more rotational inertia than a comparable gas turbine, so the system includes a control mechanism that helps prevent damage from excessive torque being applied to the distal end of the drive shaft.

The drive shaft of the present invention comprises a helically coiled wire drive shaft as is well known in the art. See, e.g., U.S. Pat. No. 6,494,890 describing such a drive shaft configuration. However, unlike the art, the present drive shaft is coiled and connected with the electric motor so that under loading conditions, the drive shaft spins open. The known art comprises drive shafts that are configured to spin-to-close. In other words, the known drive shafts, upon encountering an obstruction or other load during high-speed rotation, will wind tighter, with an increasing length and a decreasing outer diameter, until reaching a most tightly wound point.

The present invention, in contrast, comprises a drive shaft that is intended to be spun in an open direction, opposite to that of the known drive shafts, during high-speed rotation. Thus, the present drive shaft will be spinning-to-open when an obstruction or other loading at the distal end is detected and will then continue to open to a larger outer diameter than the nominal outer diameter. In further contrast to the known drive shafts, the opening drive shaft of the present invention during a loading event such as a blockage results in a shortening of the length of the drive shaft.

Advantages of such a spin-to-open system include, inter alia, the following:

1. Opening of the drive shaft during loading events helps translate torque to the electric motor, thereby allowing better more accurate torque monitoring by the control electronics;

2. The opening drive shaft during loading decreases the length of the drive shaft itself, reducing the overall loading of the drive shaft during loading events; and 3. The opening of the drive shaft during a loading event reduces the friction of the system on the guidewire, reducing the possibility that the system guidewire may be damaged during the loading event.

Consequently, one embodiment of the present invention includes a spin-to-open atherectomy system comprising a guidewire, a spin-to-open drive shaft with a nominal outer diameter and length and an electric motor for rotating the drive shaft in the spin-to-open direction at high rotational speeds.

In addition to the above functional advantages, further improvements and advantages are found in controlling the torque and/or current of the present spin-to-open system during a loading event such as a blockage.

Thus, when the controller via control electronics therein, and which is in operative connection and communication with the electric motor, detects a maximum torque applied by the electric motor to the drive shaft and/or maximum current and/or minimum rotational speed of the drive shaft, and wherein the drive shaft opens to a maximum allowed outer diameter that is correspondent to the maximum torque and/or maximum current and/or minimum rotational speed of the drive shaft, power to the electric motor is eliminated. This results in the electric motor to spin freely whereby the large angular momentum of the system may dissipate rapidly and safely, allowing the opened drive shaft to recover back to the nominal outer diameter from the maximum allowed outer diameter, without excessive torque to the drive shaft and harm to the patient.

The preceding paragraph is merely a summary, and should not be construed as limiting in any way. A more detailed description follows.

FIG. 1 is a schematic drawing of a typical known rotational atherectomy device. The device includes a handle portion 10, an elongated, flexible drive shaft 20 having an exemplary eccentric enlarged abrading head 28, and an elongated catheter 13 extending distally from the handle portion 10. The drive shaft 20 is constructed from helically coiled wire as is known in the art and the abrading head 28 is fixedly attached thereto. The catheter 13 has a lumen in which most of the length of the drive shaft 20 is disposed, except for the enlarged abrading head 28 and a short section distal to the enlarged abrading head 28. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20 (details regarding such handles and associated instrumentation are well known in the industry, and are described, e.g., in U.S. Pat. No. 5,314,407, issued to Auth, and incorporated by references herein in its entirety). The handle 10 also desirably includes a control knob 11 for advancing and retracting the turbine and drive shaft 20 with respect to the catheter 13 and the body of the handle.

The abrasive element 28 in FIG. 1 is illustrated as an eccentric solid crown, attached to the drive shaft 20 near the distal end of the drive shaft 20. The term "eccentric" is used herein to denote that the center of mass of the crown is laterally displaced away from the rotational axis of the drive shaft 20. As the drive shaft rotates rapidly, the displaced center of mass of the crown causes the drive shaft to flex radially outward in the vicinity of the crown as it spins, so that the crown may abrade over a larger diameter than its own rest diameter. Eccentric solid crowns are disclosed in detail in, for example, U.S. patent application Ser. No. 11/761,128, filed on Jun. 11, 2007 to Thatcher et al. under the title, "Eccentric abrading head for high-speed rotational atherectomy devices", published on Dec. 11, 2008 as U.S. Patent Application Publication No. US2008/0306498, and incorporated by reference herein in its entirety. Other abrading heads are within the scope of the present invention including, but not limited to concentric burrs, crowns and the like.

Figure 2:
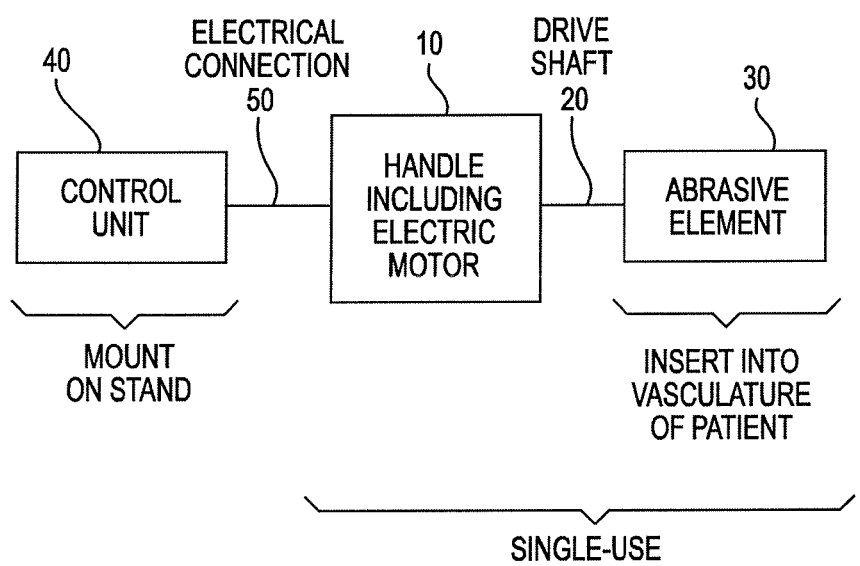
FIG. 2 shows a block diagram of the atherectomy device having an electric motor.

Turning now to FIG. 2, a block diagram of the atherectomy device having an electric motor in a handle 10, a helically coiled, spin-to-open drive shaft 20 with abrasive element 30 and connected with the electric motor 10 is illustrated.

A control unit 40 (also referred to as a controller) is the non-disposable portion of the device, and includes most of the electrical functions of the device that aren't directly related to driving the motor. For instance, the control unit 40 can recognize which type of handle is plugged into it, includes controls for setting the desired speed of the motor, and includes controls for the pump that delivers saline down the catheter.

The control unit 40 has an electrical connection 50 to the handle 10. In addition to having the control knob and the associated mechanical structure that can advance and retract the abrasive element with respect to the catheter, the handle 10 includes the actual electric motor and the mechanical coupling of the motor to the drive shaft 20.

The helically coiled, spin-to-open drive shaft 20 extends from the mechanical coupling with the motor, located in the handle 10, through the catheter to within the vasculature of the patient. The proximal (near) end of the drive shaft 20 is within the handle 10, and the distal (far) end of the drive shaft 20 extends to the blockage within the blood vessel. An abrasive element 30 is attached to, or made integral with, the drive shaft 20, and is located at or near the distal end of the drive shaft.

The handle 10, the catheter, and the drive shaft 20 are all designed for single use, and are typically disposed of once the procedure is completed, being disengageable from control unit 40. The control unit 40 is retained by the practitioner for future repeated uses.

As an alternative, the electric motor itself may be located within the control unit 40, rather than in the single-use handle 10. Locating the motor in the control unit 40 would require an additional mechanical coupling between the control unit 40 and the handle 50. The handle would still include the control knob 11 that advances and retracts the abrasive element within the catheter.

Figure 3:
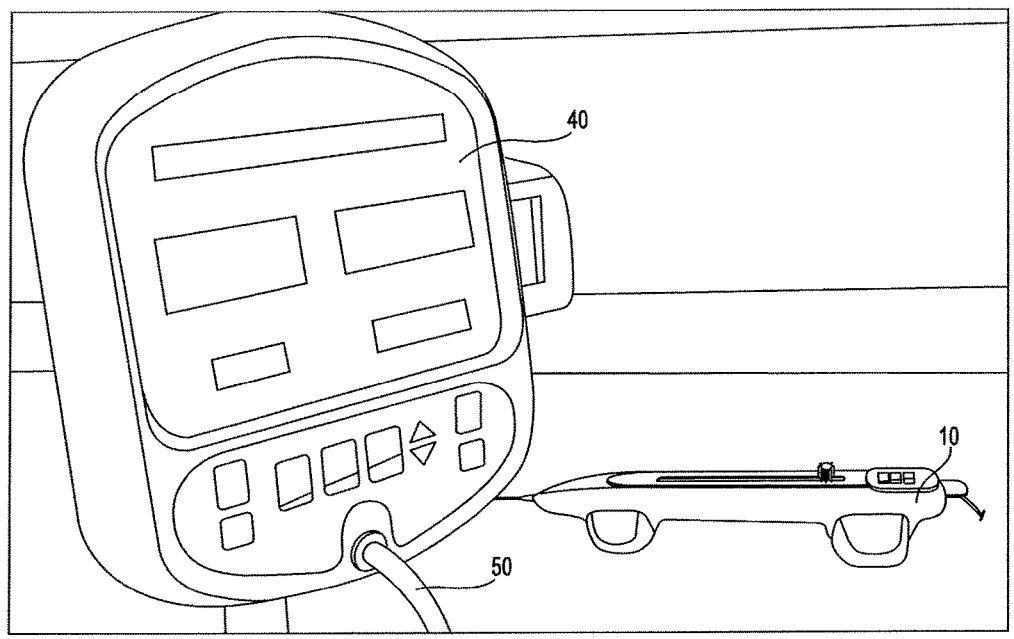
FIG. 3 is a plan drawing of an exemplary control unit and handle.

FIG. 3 is a plan view of an exemplary control unit 40 and handle 10. In this example, the electrical connection 50 comes out the front of the control unit 40 and enters the handle 10 on its right side, in the view of FIG. 3. The catheter and drive shaft attach to the left side of the handle 10, and are not shown explicitly in the view of FIG. 3.

Many of the various device features are described below, and for convenience are done so with respect to their corresponding controls on the control unit 40. It will be understood that any suitable controls, with any suitable layout on the control unit 40, may be used for the described functions, and that the controls shown in the figures are merely examples.

Figure 4:
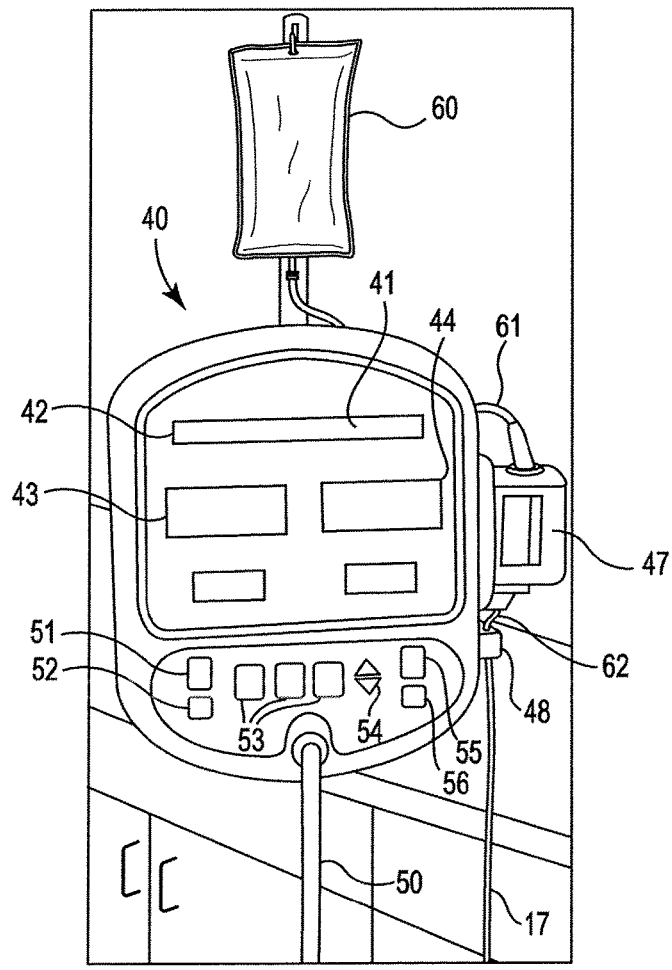
FIG. 4 is a front-view drawing of the control unit.

FIG. 4 is a front-view drawing of the control unit 40. The rear of the control unit may be placed on a counter top, clamped to a stand, hung from a pole, or may have another suitable mount. In some cases, the control unit is supported by an IV pole, so that an IV saline may be hung from higher up on the same pole and may feed a pump on the control unit 40.

Starting from the top down, the topmost element is a notification screen 41, which can display text and character messages. For instance, the screen 41 may display the status of various components, such as "saline pump off". As another example, when a particular handle is plugged in, the controller unit 40 recognizes it and may display its name and relevant information on the notification screen 41. As another example, the notification screen 41 may also display error and troubleshooting information for the practitioner.

The running speed 42 is the actual rotational velocity of the proximal end of the drive shaft, in units of 1,000 RPM (revolutions per minute), or kRPM. The running speed 42 is typically updated several times per second, and in some cases may be displayed in relatively large LEDs that are readily visible to the practitioner. Rotational speeds of up to 200 kRPM are typical.

The rotational speed may be obtained from the electric motor itself. For instance, the motor may include one or more Hall effect sensors that produce an electrical signal each time the motor rotates past a particular point. The rotational speed is proportional to the rate of the signals, or, equivalently, is inversely proportional to the time intervals between the electrical signals. Alternatively, any suitable sensors and signals may be used.

Below the actual running speed 42 is the selected speed 43, also displayed in kRPM. During operation, a control circuit (feedback loop) in the control unit 40 and/or the handle 10 adjusts the motor current and/or voltage to keep the actual running speed 42 as close as possible to the selected speed 43.

The event time 44 is the elapsed time for a particular run of the device. The event time 44 typically displays in minutes:seconds, although any suitable unit may be used.

Below the event time 44 is the total time 45, which is the cumulative total time 45 that the particular device has been operated. The motivation for such a measurement may be explained as follows.

It is typical for the atherectomy device to be rated only for a particular time, such as nine minutes, beyond which use is not recommended. In other words, a device may be repeatedly turned off and on during the course of a full procedure. Such switching off and on is permissible as long as the total cumulative time during which the device is actually on does not exceed a particular value, such as nine minutes. Typically, the handle 10 includes electronics that store the cumulative on-time, although such data may alternatively be stored in the control unit 40.

If the total operational time 45 hits the threshold value, the control unit may either shut down, or may emit a warning advising the practitioner that the on-time limit has been reached. In some cases, the limit can be overridden by the practitioner. In other cases, reaching the limit disables the motor so that the device can no longer be used.

To the right of the four speed and time displays is a pump 46 that receives saline from an external IV bag 60 and directs it into the handle 10 through the fluid supply line 17 (see FIG. 1). Once inside the handle 10, the saline is directed into the catheter 13, where it helps lubricate the drive shaft, cool the abrasive head, and flush away any debris.

It should be noted that in general, the saline from the fluid supply line 17 tends to leak a significant amount inside the handle. This leakage, although messy, is useful for lubricating and cooling the motor and the internal mechanisms of the handle, and is desirable. The leakage itself originates from slight gaps between concentric and overlapping tubes inside the handle, which form the seals. If these tubes are made to fit too snugly, the leakage may decrease, but the friction between the tubes and the rapidly rotating drive shaft may be prohibitively large. The tubes demonstrated for the electric motor device, shown and described herein, may leak only a fraction of earlier generation devices, but still leak a finite amount, and desirably so.

Saline travels from the IV bag 60, through a tube 61 to the pump 47, leaves the pump through an intermediate tube 62, passes through a void detector 48, and leaves the void detector 48 as the fluid supply line 17 (see FIG. 1).

The void detector 48 includes a light emitter, such as a light emitting diode, that shines light through the intermediate tube 62, and a photodetector diametrically across from the emitter that receives the light from the emitter. During normal operation, when the saline is flowing continuously through the intermediate tube without any bubbles, the light reaching the photodetector has a particular intensity that remains roughly constant. If the edge of a bubble passes by in the intermediate tube 62, the light reaching the photodetector is disrupted, and the photodetector output changes value. This change in value indicates that there is gas in the saline line (a "void"), and is used by the controller 40 to turn off the pump 47, in order to prevent the void from finding its way into the patient.

The button for "pump power" 51 toggles the power of the pump, from on to off, or from off to on. An LED or other indicator on or near the button may indicate if the pump is on.

The button for "prime" 52 turns on the pump, if the pump isn't already on, and sets the pump flow to a high rate, while the button is held down. The "prime" function flushes the pump system, and gets any air out of the system. The pump prime is typically used intermittently as needed.

The three buttons for "speed selection" are labeled "low", "medium" and "high", with an indicator light on each that corresponds to the selected speed. In general, for a particular model of handle 10 that is plugged into the control unit 40, there are preset speeds that are determined by the manufacturer. These speeds are automatically recognized by the control unit 40, so that the practitioner need not enter them manually. Such recognition may take place by, for instance, storage of the preset speeds on the handle 10, storage of the preset speeds in a lookup table on the control unit 40, and/or lookups-as-needed of the preset speeds through a central database, such as over the internet.

If the practitioner desired more fine control of the speed than is offered by the default low/medium/high presets, the increment buttons 54 may adjust the selected speed upward or downward by a predetermined increment, such as 10 kRPM, although any suitable increment may also be used.

The "IV bag reset" button 55 is used when a new IV bag is connected to the pump. In some cases, the user is prompted to enter the size of the IV bag. In other cases, a standard IV bag size is used. The controller 40 monitors the pump rate over time, and can effectively perform an integral of the pump rate, with respect to time, to calculate how much saline has been pumped out of the bag, and likewise, to calculate how much saline is left in the bag. When the amount of saline left in the bag drops below a predetermined threshold, the controller 40 may send a notification to the user by making a sound, flashing a light, or any other suitable notification.

Note that there is no manual control for the pump rate (or flow rate) of the pump 47. In general, the pump rate is determined at the factory, and is standardized for each rotation speed (low/medium/high), for each model of handle 10. This predetermined pump rate may be stored in a lookup table on the electronics embedded within the handle 10, may be stored in a lookup table on the electronics embedded with the control unit 40, may be calculated on the fly by the electronics in the control unit 40, may be looked up in real time from a central database, such as over the Internet, or a combination of any of the above.

The "brake override" button 56 is typically used only when something gets stuck. During normal use, the guide wire remains extended from the handle, through the center of the drive shaft, past the abrasive element, and beyond the blockage. The drive shaft then rotates over the guide wire. During use, the guide wire remains rotationally stationary, and has a "brake" in the handle 10 that locks it rotationally and prohibits its rotation. Occasionally, there may be cases when something gets stuck, whether in the catheter itself, at the distal end of the drive shaft, or beyond the distal end of the drive shaft. When something gets stuck, the user may depress the "brake override" button 56, which allows the guide wire to rotate at a very low rotational speed. In some cases, the guide wire rotates at the same low rotational speed as the drive shaft. In other cases, the guide wire rotation is independent of the rotational speed of the drive shaft. Typically, the guide wire rotates as long as the brake override button 56 is held down.

Figure 5:
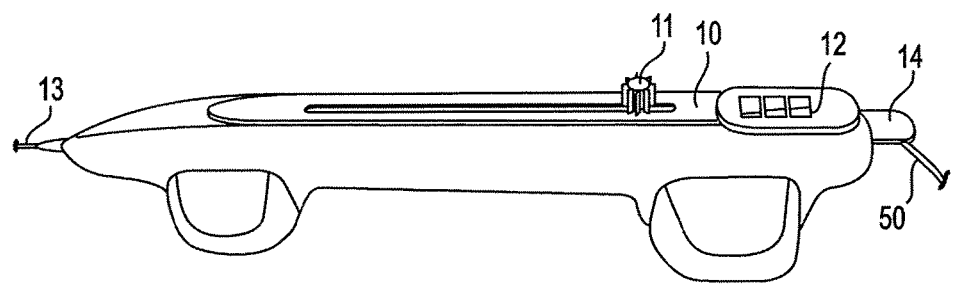
FIG. 5 is a plan drawing of the handle.

FIG. 5 is a plan drawing of a typical handle 10. The electrical connection 50 from the control unit 40 enters the handle 10 on the right side of FIG. 5. The catheter and drive shaft leave the handle 10 on the left side of FIG. 5. As with the controller, the layout of the controls is merely exemplary, and other suitable layouts may be used.

The control knob 11 longitudinally translates the drive shaft with respect to both the guide wire and the catheter, which remain stationary. The knob 11 slides along a channel with a travel range of about 15 cm. The control knob 11 is used extensively during the procedure, during which the practitioner positions and repositions the rapidly spinning abrasive head to fully remove the blockage in the blood vessel.

The control knob 11 may also include an optional on/off toggle button, which may turn on and off the electric motor in the handle.

The handle 10 may include a duplicate set of speed selection buttons 12, which can repeat the functionality of the corresponding buttons 53 on the controller. Having speed selection buttons 12 on the handle 10 itself is a great convenience for the practitioner.

Lever 14 is a brake for the guide wire, which, when engaged, prevents rotation of the guide wire as the drive shaft is rotated. In some cases, the guide wire brake 14 is locked when the lever is horizontal, as in FIG. 5, and is unlocked when pulled upward by the practitioner.

Figure 6:
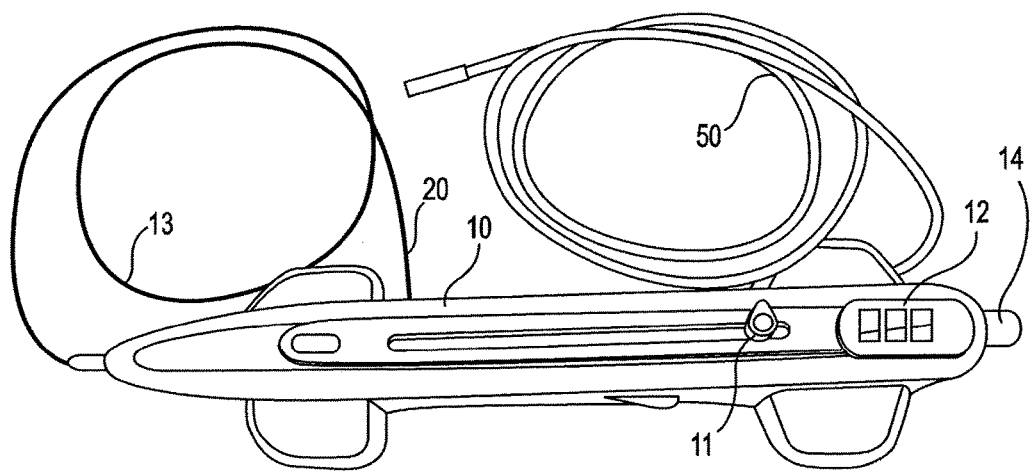
FIG. 6 is a top-view drawing of the handle of FIG. 5.

FIG. 6 is a top-view drawing of the handle 10 of FIG. 5. In addition to showing the control knob 11, the speed selection buttons 12 and the guide wire brake 14, FIG. 6 shows the electrical connection 50, which is typically a 14-foot-long cable although other suitable lengths may be used, and shows the catheter 13, typically connected to the body of the handle 10 with a strain relief. The distal end of the drive shaft 20 is visible in FIG. 6, and is shown in more detail in FIG. 7.

Figure 7:
FIG. 7 is a top-view drawing of the distal end of the drive shaft, extending beyond the distal end of the catheter.

FIG. 7 is a top-view drawing of the distal end of the drive shaft 20, extending beyond the distal end of the catheter 13. The drive shaft 20 is typically a helically-wound coil of wire, although any suitable mechanism for delivering torque from the electric motor to the abrasive element 28 may be used as a drive shaft. For instance, an alternative drive shaft may be a solid or slotted tube of plastic or metal.

The abrasive element 28 shown in FIG. 7 is attached to the drive shaft 20, with an abrasive material coated on the exterior of the abrasive element 28. Alternatively, any suitable abrasive element may be used, including an element (a so-called "crown") having a center of mass that is laterally displaced from the rotational axis of the drive shaft (a so-called "eccentric" crown) and having an abrasive exterior or the abrasive element 28 may be concentric with a center of mass located on the rotational axis of the drive shaft. The eccentric solid crown is typically attached to the drive shaft, although it may alternatively be made integral with the drive shaft. The eccentric solid crown is typically attached near, but not at, the distal end of the drive shaft, although it may alternatively be attached at the distal end of the drive shaft.

Figure 8:
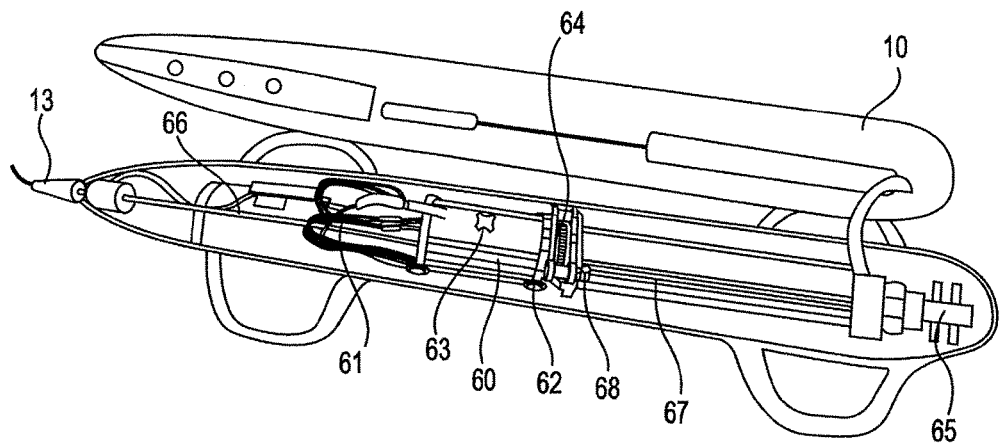
FIG. 8 is a top-view drawing of the handle of FIGS. 5 and 6, opened for clarity.
Figure 9:
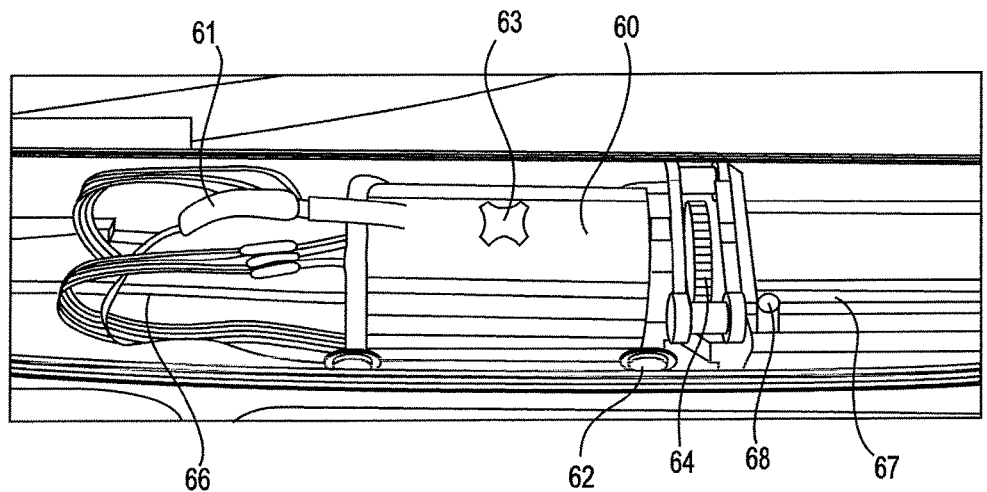
FIG. 9 is a close-up view of the carriage inside the handle of FIG. 8.

FIG. 8 is a top-view drawing of the handle 10, which is opened for clarity. FIG. 9 is a close-up view of the carriage inside the handle 10 of FIG. 8. In practice, the handle remains closed before, during and after the procedure. As with FIGS. 5 and 6, the catheter 13 and drive shaft 20 exit the left edge of the handle 10 in the view of FIG. 8.

The electric motor itself resides within a carriage 60. The exterior of the carriage 60 functions as a heat sink for the motor. The motor is powered by a series of electrical connections 61, which connect to the electrical connection 50 that in turn connects to the control unit 40.

The motor can travel longitudinally with a 15 cm range of travel, and does so being mounted on wheels 62 that engage respective tracks within the handle. Alternatively, other translating mechanism may be used. The handle is typically used for a single procedure and then disposed, so the wheels and tracks should be sturdy, but generally need not be designed for an especially long lifetime.

The carriage has an optional on/off toggle switch 63 on its top, which corresponds to the off/off button on the control knob 11. During use, the control knob 11 is directly above the toggle switch 63, and the practitioner may depress the knob 11 to turn the motor on and off.

There may be one or more gears 64 that step up or step down the rotation between the motor and the drive shaft. For instance, the motor itself may only have a maximum rotational speed of 50 kRPM, and a series of differently-sized gears may step the rotation up 4× to 200 kRPM for the drive shaft.

An advantage to having a geared system is that the guide wire may be routed through the center of a gear, rather than through the center of the motor. This simplifies the mechanical system.

Element 65 is another on/off switch, much like the toggle switch 63. One difference, however, is that the switch 65 is linked to the guide wire brake level 14. When the brake is released, the level is in the up position, and the switch 65 shuts off the motor, regardless of the state of any other on/off switches. When the brake is engaged, the switch 65 allows any other switch to toggle the motor on and off. There is accompanying circuitry for the switch 65, also located at or near the rightmost edge of the handle in FIG. 8.

Elements 66, 67 and 68 involve mechanical aspects of keeping the rapidly spinning drive shaft contained and stable, and of ensuring functional seals to keep fluids contained adequately. Elements 66 and 67 are telescoping mechanisms, such as concentric hypo tubes, which are tight enough to provide adequate fluid seals, and loose enough so that they do not rob the system of torque due to excessive friction.

As noted above, the interior of the handle 10 is not a perfectly dry system. The vapor and small amount of leaked liquid (saline) serves to cool the motor and the other moving parts in the handle and in the catheter. The front foot of the system (leftmost foot in FIG. 8) may be hollow and open, so that fluid can collect in it. The rear foot of the system (rightmost foot in FIG. 8) may include the CPU of the handle, which may be sealed between various foams and glues so that it doesn't get wet during use.

The motor and gears, spinning the drive shaft up to 200 kRPM, may produce significant vibrations inside the handle. In general, these vibrations are undesirable, and it is generally preferable to dampen these vibrations whenever possible. The telescoping portions, extending from the proximal edge of the handle to the carriage, and from the carriage to the distal edge of the handle, have their own resonant frequencies. The resonant frequencies of the portions can vary, depending on where in the range of travel the carriage actually is. As a result, completely avoiding a resonant frequency during use is generally difficult or impossible. One way to dampen the vibrations for a large range of resonant frequencies is to use one or more strain reliefs 68 within the coupling between carriage and telescopes.

Having described the mechanical structure of the electric motor and controller, we turn first to the unforeseen obstacles and then to the unforeseen advantages of replacing the known gas turbine with an electric motor.

The known gas turbines were generally small, plastic pieces that could be sped up to 200 kRPM using air pressure. The turbines themselves were generally small, easy to work with and had desirable mechanical characteristics, but the air-pressure-controlling systems that fed the turbines were expensive, cumbersome, and mechanically quite complicated. Swapping an old gas turbine out for an electrical motor presents some design and control challenges.

First, the rotational inertia of the electric motor can be up to 10 times larger than that of the tiny plastic gas turbine, or more. This presents serious challenges for the control system that controls the motor; simply using the old control system from the turbine will not work.

A typical control system for the gas turbine is as follows. A fiber optic at the turbine provides the actual rotational speed to the control system, which adjusts the pressure of the gas periodically to match the rotational speed to a desired speed. The control system can adjust the pressure up to a particular threshold value, such as 64 psi. If after a predetermined time, the turbine is not spinning at its desired rotational speed, the control system assumes that something is impeding the rotation of the abrasive element, so the pressure is set to zero and the turbine stops. Similarly, if the fiber optic detects that the turbine is stopped, the control system assumes that the distal end of the drive shaft is caught up something, so the pressure is also set to zero.

It is instructive to examine the torques experienced by the abrasive element at the distal end of the drive shaft, when such a shutdown occurs. In particular, consider the case where the distal end of the drive shaft becomes caught on something, and it stops suddenly.

Initially, just after being caught, there is no torque at the abrasive element. From this zero value, the torque rises rapidly, since the turbine and the entire drive shaft are rotating, while the distal end of the tip remains stuck.

Eventually, the torque peaks, which occurs when the drive shaft is momentarily stationary. At this peak, all the angular momentum that was present in the previously-spinning drive shaft is converted into torque, by angularly compressing the drive shaft to its most compressed state.

Beyond this peak, the torque starts falling, as some of the angular compression pushes back on the turbine. During this stage, the distal end of the drive shaft remains stationary (because it's stuck), and the rest of the drive shaft, which extends back to its proximal end at the turbine, rotates in the opposite direction as the first stage described above.

Eventually, the angular compression is dissipated and the torque plateaus. At this plateau, the drive shaft is stationary throughout, but is angularly compressed in a steady-state by the angular force (torque) of the turbine. The plateau torque value is larger than zero, but smaller than the first peak described above. Using the control mechanism described above, the torque remains at this plateau value for about four seconds (minus the rise and settling time, which is typically in the range of milliseconds), and then the gas pressure to the turbine is shut off.

Figure 10:
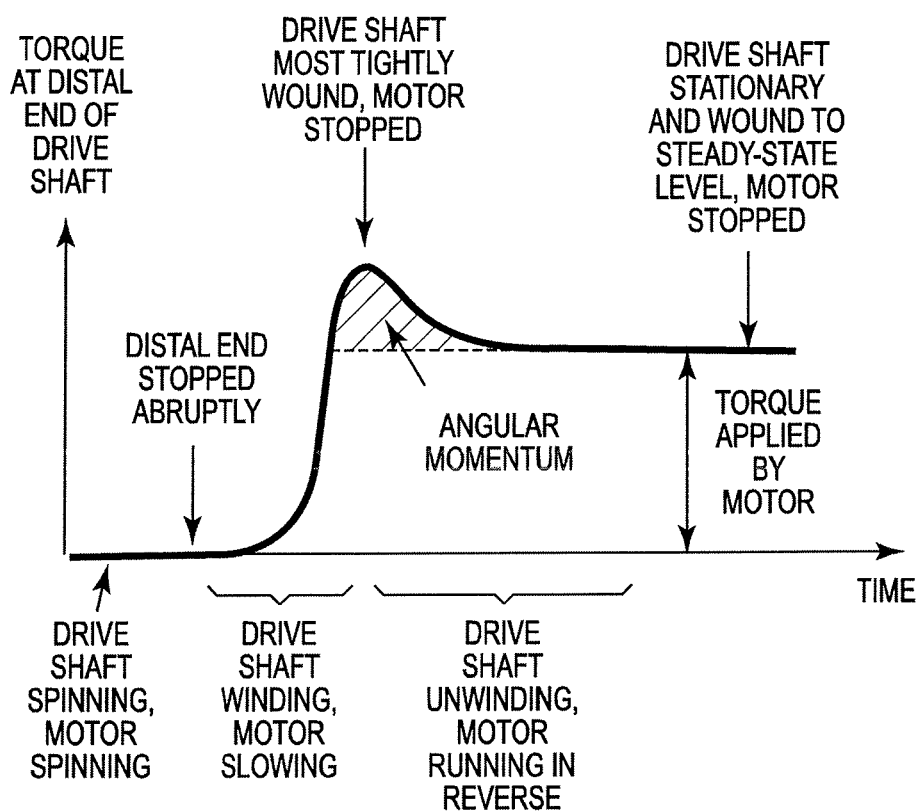
FIG. 10 is a plot of torque at the distal end of the drive shaft versus time for a distal end obstruction, for the known gas turbine.

This is all shown in the plot of FIG. 10. The cross-hatched area under the large peak is the angular momentum of the motor, plus the angular momentum of the drive shaft and of any intervening components. For the known gas turbines, this value is acceptably small, and doesn't cause any problems. However, for the electric motors, the motor itself has much more angular momentum than any other components in the system, and this value can be much larger, by a factor of up to 10 or more. If the same control system were used with the electric motor, the large peak would be much larger, on the order of 10 times larger, if it scales with the angular momentum of the motor. This huge increase in torque would likely cause damage to the instrument, or worse, damage to the blood vessel in the patient. This is unacceptable.

One way to deal with the large angular momentum issue is to change the way the motor is handled once a blockage is detected. For the known gas turbines, it was adequate to wait four seconds, then cut off the gas pressure feeding the turbine. For the electric motor, however, there could be a great deal of damage in those four seconds.

Figure 11:
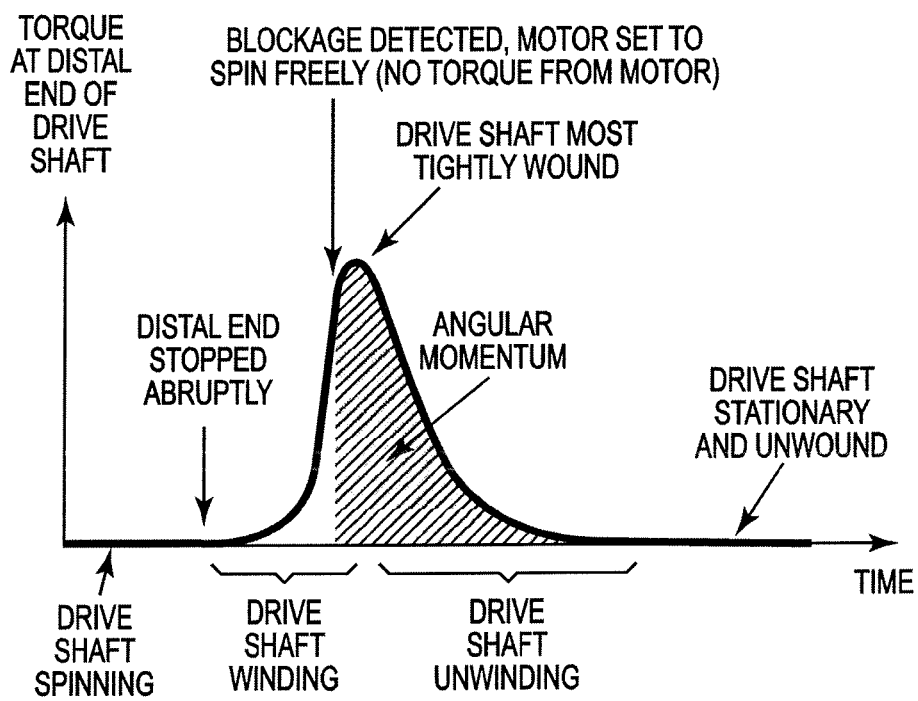
FIG. 11 is a plot of torque at the distal end of the known spin-to-close drive shaft versus time for a distal end obstruction, for the electric motor.

One approach for quickly dissipating the angular momentum of the electric motor with a spin-to-close drive shaft and controller is shown schematically FIG. 11.

Initially, the device is working normally. The motor is applying a torque to the proximal end of the drive shaft, the drive shaft is spinning along with the motor, and the distal end of the drive shaft is spinning.

The device then encounters an obstruction that grabs the distal end of the drive shaft, causing it to stop rotating. On FIG. 11, this is the point labeled "distal end stopped abruptly".

The distal end of the drive shaft is stopped, but the motor continues to rotate the proximal end of the drive shaft. The drive shaft begins to wind up (compress rotationally), and the torque required to perform such winding gradually slows down the motor.

Once the motor rotation falls below a particular threshold, which can be a fixed value below the desired rotation speed and/or a percentage drop from the desired rotation, the control unit decides that an obstruction has been detected. The control unit responds by releasing the motor and allowing it to spin freely as a flywheel. On FIG. 11, this occurs at the point labeled "blockage detected, motor set to spin freely (no torque from motor)".

The drive shaft continues to wind up (compress rotationally), under the influence of the angular momentum of the free-spinning motor. At some point, all the rotational kinetic energy from the angular momentum is converted to rotational potential energy, and the drive shaft reaches its most tightly wound point.

The drive shaft then unwinds, converting essentially all of its rotational potential energy into rotational kinetic energy and spinning the free-spinning motor in the opposite direction. On FIG. 11, this occurs in the region labeled "drive shaft unwinding".

Note that there are likely some oscillations in this portion, where the curve oscillates about zero with decreasing amplitude over time (damped oscillations). Eventually, the curve settles to a steady-state at zero, where the drive shaft is essentially unwound and stationary, the motor is essentially stationary, and there is no torque applied to the end of the distal end of the drive shaft. This is a relaxed, steady-state condition, where all of the kinetic and potential energy has been dissipated through friction and other losses.

Note that the horizontal time axis of FIG. 11 is not necessarily the same as that in FIG. 10. In practice, the settling time of FIG. 11 is on the order of milliseconds.

There are two quantities of note in FIG. 11.

First, the peak value of the solid curve is the maximum torque that is applied at the distal end of the drive shaft. If this maximum torque exceeds a particular value, there may be damage to the instrument, or worse, damage to the blood vessel of the patient. It was found in practice that the peak value for the gas turbine, shown schematically in FIG. 10, was low enough so that it didn't cause any damage. For the electric motor, shown in FIG. 11, the control algorithm attempts to keep the peak torque value at or below that shown in FIG. 10 for the gas turbine, with the logic that if that torque value didn't cause any problems for the turbine, it shouldn't cause any problems for the electric motor either.

Second, the cross-hatched region represents the angular momentum of the electric motor, the drive shaft and the accompanying coupling elements. In practice, the electric motor completely overshadows the other contributions. This "area under the curve" is essentially a fixed quantity for a particular motor and rotation speed, and it is the job of the control algorithm to "smooth" that area out along the horizontal axis, while ensuring that the peak torque doesn't exceed a particular value. The challenge of the electric motor is that the cross-hatched area is significantly larger than for the gas turbine, by a factor of up to 10 or more.

In contrast, the present invention comprises a spin-to-open drive shaft 20 monitored for loading events, e.g., a blockage, by a controller connected with the electric motor. A loading event is illustrated in FIG. 12 for the spin-to-open drive shaft system.

Thus, in FIG. 12, the helically coiled drive shaft 20 described herein is arranged in a spin-to-open direction. The x-axis represents time and the y-axis represents torque applied to the drive shaft by the electric motor and/or current used by the electric motor.

Beginning at time 0, and as designated by section "A" on the Figure, the drive shaft is accelerated to the desired rotational speed, typically high-rotational speeds are desired as well known to the skilled artisan for these procedures. At the desired speed, the drive shaft will have an nominal outer diameter that is essentially the same as the outer diameter of the drive shaft at rest and without any torqueing or loading on the drive shaft.

When an obstruction is encountered, as designed by section "B", the drive shaft will begin loading and may stop rotating at its distal end, the point at which the blockage or obstruction is encountered by the rotating drive shaft. As seen in section C in the graph of FIG. 12, this in turn causes the drive shaft to begin to open, resulting in an increase in outer diameter, torque and/or current, with a possible slowing of rotational speed in some cases or embodiments. If, as in FIG. 12, the blockage continues to stop the distal end of the drive shaft from rotating, the outer diameter of the drive shaft continues to increase, ultimately reaching a maximum allowed outer diameter and the corresponding minimum drive shaft length, a point marked as 100 on the graph which, as shown in section D, is correspondent with the maximum allowed torque and/or current. 100 may also correspondent with the minimum allowed rotational speed.

Thus, at the same time the outer diameter of the drive shaft is increasing to its maximum, the applied torque and/or current of the electric motor is also increasing to a maximum allowed threshold, correspondent with 100 in FIG. 12. At this point, rotational speed may remain constant, without measurable slowing of the electric motor, until the control electronics eliminate power to the electric motor at point 102 as illustrated in FIG. 12 after predetermined time interval 104, so that no torque-induced or current-induced rotation is provided by the electric motor to the drive shaft. In this case, as illustrated, rotational speed of the drive shaft decreases and ceases at point 102 or very shortly thereafter. Alternatively, if the rotational speed drops below the allowed minimum threshold limit given the prevailing torque and current, power to the electric motor may be eliminated because a blockage may be indicated.

Once the power to the electric motor is eliminated, no further torque, current-induced or otherwise, is delivered or transferred from the electric motor to the drive shaft and, therefore, the electric motor allows the drive shaft to spin freely to dissipate the energy stored in the drive shaft when at its maximum outer diameter. The drive shaft, once opened to its maximum allowable outer diameter, now may safely return to its smaller nominal outer diameter.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

We claim:

1. A spin-to-open rotational atherectomy system, comprising:
   an elongated, flexible helically coiled drive shaft having a distal end for insertion into a vasculature of a patient and having a proximal end opposite the distal end remaining outside the vasculature of the patient and having a lumen therethrough, the helical coils of the drive shaft configured to enable the drive shaft to rotate in a spin-to-open direction during high-speed rotation, the drive shaft having a nominal outer diameter and length and a maximum allowed outer diameter limit, wherein when the drive shaft encounters a blockage, the outer diameter increases and the length decreases;

a guidewire adapted to translate and rotate within the lumen of the drive shaft and to allow the drive shaft to translate and rotate over the guidewire;

an abrasive crown attached to the drive shaft proximate the distal end of the drive shaft;

an electric motor rotatably coupled to the proximal end of the drive shaft, the electric motor being capable of rotating the drive shaft in the spin-to-open direction; and a control unit comprising control electronics adapted to monitoring and controlling the rotation of the electric motor and drive shaft and comprising a maximum limit for torque applied by the electric motor to the drive shaft, a maximum current limit used by the electric motor and a minimum rotational speed limit for the rotating drive shaft, wherein the maximum limits for torque, maximum current and minimum rotational speed are correspondent with the maximum limit for the outer diameter of the drive shaft, wherein the control electronics eliminate power to the electric motor when the maximum limit of the outer diameter of the drive shaft is reached during a loading event so that no torque or current-induced rotation is transferred from the electric motor to the drive shaft.

2. The rotational atherectomy system of claim 1, wherein the outer diameter of the drive shaft returns to the nominal outer diameter after the power is eliminated to the electric motor.

3. The rotational atherectomy system of claim 1,
wherein the electric motor is contained within a handle; and
wherein the control electronics are contained in a control unit separate from the handle and electrically tethered to the handle.

4. The rotational atherectomy system of claim 1, wherein the control unit includes internal memory for storing performance specifications.

5. The rotational atherectomy system of claim 1, wherein the control unit includes an external activation control and an external electric motor rotational speed control.

6. The rotational atherectomy system of claim 1, wherein the control unit is simultaneously operable with an electronic heart defibrillator.

7. The rotational atherectomy system of claim 1, wherein the control unit includes a void detector that ensures reliable delivery of saline to the vasculature of the patient.

8. The rotational atherectomy system of claim 1,
wherein the abrasive crown comprises an eccentric solid crown attached to the drive shaft and that has a center of mass that is laterally displaced from a rotational axis of the drive shaft; and
wherein the eccentric solid crown includes an abrasive exterior surface.

* * * * *